United States Patent
Fujioka

(10) Patent No.: US 12,072,308 B2
(45) Date of Patent: Aug. 27, 2024

(54) CULTURE DEVICE

(71) Applicant: SCREEN HOLDINGS CO., LTD., Kyoto (JP)

(72) Inventor: Ryota Fujioka, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 17/850,287

(22) Filed: Jun. 27, 2022

(65) Prior Publication Data

US 2023/0018813 A1 Jan. 19, 2023

(30) Foreign Application Priority Data

Jul. 14, 2021 (JP) .................... 2021-116675

(51) Int. Cl.
*G01N 27/04* (2006.01)
*G01N 33/483* (2006.01)

(52) U.S. Cl.
CPC ......... *G01N 27/04* (2013.01); *G01N 33/4833* (2013.01)

(58) Field of Classification Search
CPC ...... G01N 27/04; G01N 33/487; G01N 33/48; G01N 33/5005; G01R 27/02; G01R 27/08; G01R 27/14
See application file for complete search history.

(56) References Cited

U.S. PATENT DOCUMENTS

2010/0029506 A1* 2/2010 Wang ..................... G01N 27/02
506/10
2015/0185173 A1* 7/2015 Potyrailo ............... C12M 41/36
435/39

FOREIGN PATENT DOCUMENTS

| EP | 2 950 086 A1 | 12/2015 |
| JP | 2005-137307 A | 6/2005 |
| JP | 2020-146015 A | 9/2020 |
| WO | 2020/208229 A1 | 10/2020 |

(Continued)

OTHER PUBLICATIONS

Platypus Technologies, An Overview of the Fabrication Processes for Interdigitated Electrodes, Published 2022, https://www.platypustech.com/fabricating-interdigitated-electrodes (Year: 2022).*

(Continued)

*Primary Examiner* — Son T Le
*Assistant Examiner* — Brian Butler Geiss
(74) *Attorney, Agent, or Firm* — Rimon P.C.

(57) ABSTRACT

A culture device is applicable to measurement of an electrical resistance of cells. The culture device includes a measurement chamber, a permeable layer, an upper working electrode, and a lower working electrode. The measurement chamber is longer in a first direction than in a second direction intersecting the first direction. The permeable layer partitions the measurement chamber into a first chamber on an upper side and a second chamber on a lower side. The permeable layer is permeable to liquid. The upper working electrode is disposed on the upper side with respect to the measurement chamber, and has working electrode portions longer in the first direction than in the second direction. The lower working electrode is disposed on the lower side with respect to the measurement chamber, and has working electrode portions longer in the first direction than in the second direction.

10 Claims, 9 Drawing Sheets

(56) References Cited

FOREIGN PATENT DOCUMENTS

WO       2021/065287 A1    4/2021
WO    WO-2021065287 A1 *   4/2021   ............ C12M 23/20

OTHER PUBLICATIONS

Extended European Search Report issued in corresponding European Patent Application No. 22182962.5-1111, dated Dec. 9, 2022.

* cited by examiner

FIG. 7

| RESISTANCE [Ω] | | | | |
|---|---|---|---|---|
| UNIFORM RESISTANCE IN ENTIRE AREA | A1_1/10 | A1_1/100 | A2_1/10 | A2_1/100 |
| 220.7 | 197.5 | 190.6 | 197.9 | 191.3 |

CULTURE DEVICE

RELATED APPLICATIONS

This application claims the benefit of Japanese Application No. 2021-116675, filed on Jul. 14, 2021, the disclosure of which is incorporated by reference herein.

BACKGROUND OF THE INVENTION

Field of the Invention

The subject matter disclosed herein relates to a culture device.

Description of the Background Art

For investigation of the properties of cultures such as cultured cells and the state of the cultures, there has been known a technique of measuring the electrical resistance of the cultures. For example, in transepithelial electrical resistance (TEER) measurement, electrodes are placed on one side and the other side of a membrane for cell culture in a culture solution, and the electrical resistance between the electrodes is measured. This measures the electrical resistance of the cells cultured on the membrane. Such a technique of measuring the electrical resistance of cells is disclosed, for example, in Japanese Patent Application Laid-Open No. 2005-137307.

Japanese Patent Application Laid-Open No. 2020-146015 discloses a microfluidic device in which a permeable membrane for culturing cells is placed in a flow channel, and multiple pairs of electrodes are placed above and below the permeable membrane. In Japanese Patent Application Laid-Open No. 2020-146015, upper working electrodes and lower working electrodes extend in a transverse direction of the flow channel, and are placed to transverse the flow channel.

In the TEER measurement, it is desirable that current is applied uniformly to the entire cultures in a measurement chamber. When electrodes are placed to transverse the flow channel as in Japanese Patent Application Laid-Open No. 2020-146015, it is contemplated to increase the width of the electrodes in a longitudinal direction of the flow channel in order to apply current to a wide area in the flow channel. In this case, however, there has been apprehension that the electrodes become a hindrance to the observation of the cultures due to the increased width of the electrodes. It is also contemplated to arrange multiple electrodes in the longitudinal direction of the flow channel in order to apply current to a wide area in the flow channel. In this case, however, there has been apprehension that the electrodes become a hindrance to the observation of the cultures due to the increase in the number of electrodes.

SUMMARY OF THE INVENTION

It is therefore an object of the present invention to provide a technique for effectively applying current to a wide area of a measurement chamber while preventing electrodes from becoming a hindrance to the observation of cultures.

To solve the aforementioned problem, a first aspect of the present invention is intended for a culture device applicable to measurement of an electrical resistance of a culture. According to the first aspect of the present invention, the culture device comprises: a measurement chamber longer in a first direction than in a second direction intersecting the first direction; a permeable layer partitioning the measurement chamber into a first chamber on a first side and a second chamber on a second side as seen in a third direction, the third direction intersecting the first and second directions, the permeable layer being permeable to liquid; a first-side working electrode disposed on the first side as seen in the third direction with respect to the measurement chamber, and having an electrode portion longer in the first direction than in the second direction; and a second-side working electrode disposed on the second side as seen in the third direction with respect to the measurement chamber, and having an electrode portion longer in the first direction than in the second direction.

In the culture device according to the first to eleventh aspects, the first-side working electrode is disposed in the measurement chamber so as to extend in the longitudinal direction of the measurement chamber. This allows current to be effectively applied to a wide area of the measurement chamber while preventing the first-side working electrode from becoming a hindrance to the observation of the culture.

A second aspect of the present invention is intended for the culture device of the first aspect, wherein the second-side working electrode has a first second-side working electrode portion extending in the first direction and facing the first-side working electrode in the measurement chamber.

In the culture device according to the second aspect, the first second-side working electrode portion faces the first-side working electrode. This allows current to be effectively applied to the culture between the first-side working electrode and the second-side working electrode.

A third aspect of the present invention is intended for the culture device of the first or second aspect, wherein the second-side working electrode has a second second-side working electrode portion extending in the first direction and spaced from the first-side working electrode in the second direction in the measurement chamber.

In the culture device according to the third aspect, the second second-side working electrode portion is spaced from the first-side working electrode in the second direction. Thus, the range in which current flows is extended in the second direction.

A fourth aspect of the present invention is intended for the culture device of the first aspect, wherein the first-side working electrode includes: a first first-side working electrode portion extending in the first direction; and a second first-side working electrode portion extending in the first direction and spaced from the first first-side working electrode portion in the second direction.

In the culture device according to the fourth aspect, the range to which current is applied is extended in the second direction.

A fifth aspect of the present invention is intended for the culture device of the fourth aspect, wherein the second-side working electrode includes: a first second-side working electrode portion extending in the first direction; and a second second-side working electrode portion extending in the first direction and spaced from the first second-side working electrode portion in the second direction.

In the culture device according to the fifth aspect, the range in which current flows is extended in the second direction.

A sixth aspect of the present invention is intended for the culture device of the fifth aspect, wherein the first first-side working electrode portion faces the first second-side working electrode portion in the measurement chamber.

In the culture device according to the sixth aspect, current is applied to the culture between the first first-side working electrode portion and the first second-side working electrode portion.

A seventh aspect of the present invention is intended for the culture device of the sixth aspect, wherein the second first-side working electrode portion faces the second second-side working electrode portion in the measurement chamber.

In the culture device according to the seventh aspect, current is applied to the culture between the second first-side working electrode portion and the second second-side working electrode portion.

An eighth aspect of the present invention is intended for the culture device of any one of the fifth to seventh aspects, wherein a second distance is 1.5 times a first distance, the first distance being a distance between the first first-side working electrode portion and the first second-side working electrode portion, the second distance being a distance between the first first-side working electrode portion and the second second-side working electrode portion.

In the culture device according to the eighth aspect, the density of current applied to the culture between the first first-side working electrode portion and the second second-side working electrode portion is made closer to the density of current applied to the culture between the first first-side working electrode portion and the first second-side working electrode portion. This makes the density of current applied to the culture uniform in the second direction.

A ninth aspect of the present invention is intended for the culture device of any one of the first to eighth aspects, which further comprises: a first-side reference electrode disposed on the first side as seen in the third direction with respect to the measurement chamber, and having an electrode portion longer in the first direction than in the second direction; and a second-side reference electrode disposed on the second side as seen in the third direction with respect to the measurement chamber, and having an electrode portion longer in the first direction than in the second direction.

In the culture device according to the ninth aspect, current is applied between the first first-side working electrode portion and the first second-side working electrode portion, and voltage between the first-side reference electrode and the second-side reference electrode is measured, whereby TEER measurement by means of a four-terminal method is performed.

A tenth aspect of the present invention is intended for the culture device of any one of the first to ninth aspects, which further comprises: a first member having an inner surface forming the first chamber; a second member disposed on the second side as seen in the third direction with respect to the first member and having an inner surface forming the second chamber; a first-side electrode base material disposed on the first side as seen in the third direction with respect to the first member and having a surface on which the first-side working electrode is disposed; and a second-side electrode base material disposed on the second side as seen in the third direction with respect to the second member and having a surface on which the second-side working electrode is disposed, the permeable layer being disposed between the first member and the second member.

In the culture device according to the tenth aspect, the first member, the second member, the first-side electrode base material, the second-side electrode base material, and the permeable layer are stacked in a predetermined order, whereby the measurement chamber with the working electrodes disposed on both sides is easily formed.

An eleventh aspect of the present invention is intended for the culture device of any one of the first to tenth aspects, wherein the first-side working electrode has an electrode portion extending from a first end of the measurement chamber to a second end thereof as seen in the first direction, and wherein the second-side working electrode has an electrode portion extending from the first end of the measurement chamber to the second end thereof as seen in the first direction.

In the culture device according to the eleventh aspect, the first-side working electrode has the electrode portion extending from the first end of the measurement chamber to the second end thereof as seen in the first direction. This allows current to be applied to the entire longitudinal area of the measurement chamber.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 shows the resistances of cells calculated from the simulation results of current density using the analytical model of FIGS. 6A to 6D;

DESCRIPTION OF THE PREFERRED EMBODIMENTS

Figure 1:
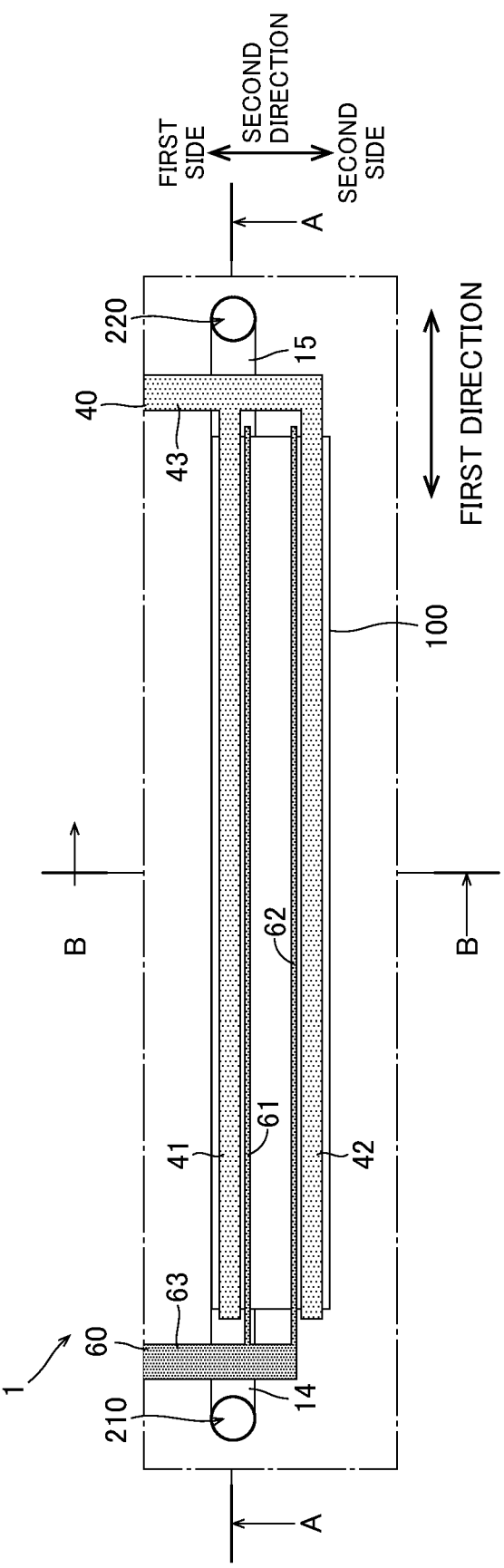
FIG. 1A is a top view of a culture device according to a preferred embodiment.
FIG. 1B is a bottom view of the culture device according to the preferred embodiment.

A preferred embodiment according to the present invention will now be described with reference to the drawings. Components described in the preferred embodiment are merely illustrative, and there is no intention to limit the scope of the present invention thereto. In the drawings, the dimensions of components and the number of components are shown in exaggeration or in simplified form, as appropriate, for the sake of easier understanding in some cases.

1. Preferred Embodiment

Figure 2:
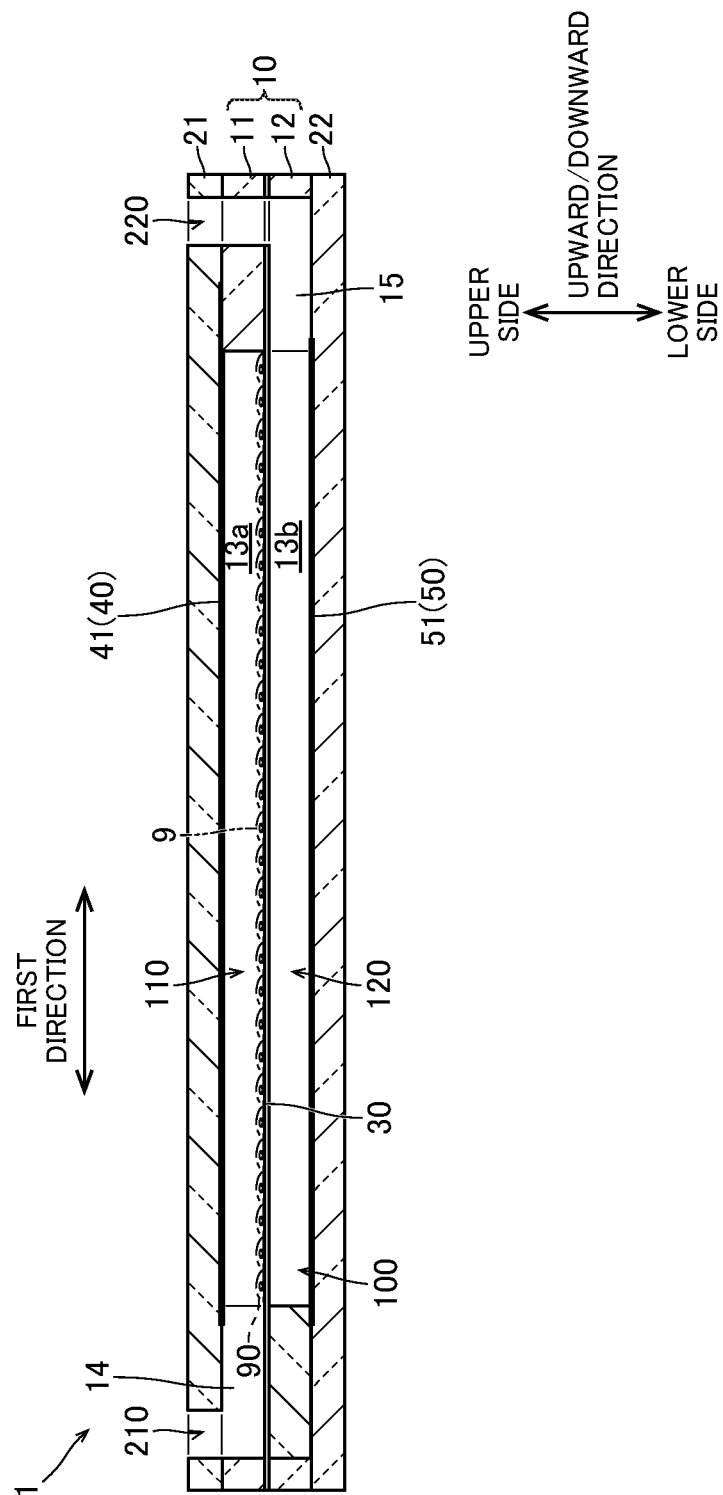
FIG. 2 is a sectional view of the culture device taken along a line A-A of FIG. 1A.

FIG. 1A is a top view of a culture device 1 according to a preferred embodiment, and FIG. 1B is a bottom view of the culture device 1 according to the preferred embodiment. In FIGS. 1A and 1B, structures of a measurement chamber 100 and the surroundings of the measurement chamber 100 are shown in the culture device 1. FIG. 2 is a sectional view of the culture device 1 taken along a line A-A of FIG. 1A, and FIG. 3 is a sectional view of the culture device 1 taken along a line B-B of FIG. 1A.

In the following description, a "first direction", a "second direction", and an "upward/downward direction (third direction)" are defined for purposes of illustrating the positional relationship of components. The second direction intersects the first direction, and more preferably is orthogonal to the first direction. The upward/downward direction intersects the first and second directions, and more preferably is orthogonal to the first and second directions. In the following description, an upper side as seen in the upward/downward direction is referred to simply as an "upper side" and a lower side as seen in the upward/downward direction is referred to simply as a "lower side" in some cases.

As shown in FIGS. 1A and 1B, the culture device 1 is what is called a microchannel device in which the measurement chamber 100 that is an internal space is a closed space except for a fine supply flow channel 14 and a fine discharge flow channel 15. The culture device 1 is applied to TEER measurement which measures the electrical resistance (resistance, reactance, or impedance) of cells 9 (cultures) cultured in the measurement chamber 100 by means of a four-terminal method. It should be noted that the cultures to be measured are not limited to the cells 9, but may be biological samples such as living tissues.

Figure 3:
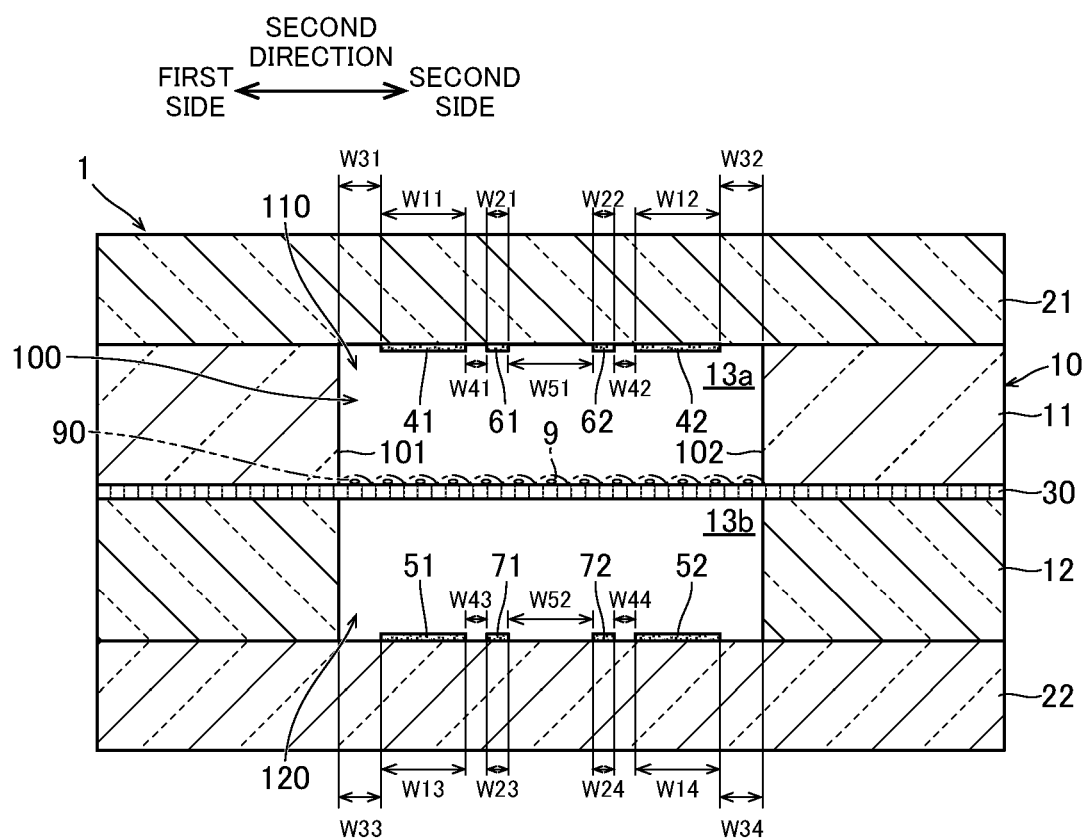
FIG. 3 is a sectional view of the culture device taken along a line B-B of FIG. 1A.

As shown in FIGS. 2 and 3, the culture device 1 includes a measurement container 10, an upper electrode base material 21 (a first-side electrode base material), and a lower electrode base material 22 (a second-side electrode base material). The measurement container 10 includes a plate-like first member 11, and a second member 12. The second member 12 is disposed on the lower side of the first member 11. The first member 11 and the second member 12 are made of, for example, PET (polyethylene terephthalate).

The measurement container 10 has the measurement chamber 100 therein. The measurement chamber 100 forms a space that can accommodate a liquid such as a culture solution. Side surfaces of the measurement chamber 100 are formed by inner surfaces 13a and 13b of through holes formed in the first and second members 11 and 12. As shown in FIG. 3, the measurement chamber 100 has a first side surface 101 on a first side as seen in the second direction, and a second side surface 102 on a second side as seen in the second direction. The first side surface 101 and the second side surface 102 face each other in the second direction.

As shown in FIGS. 1A and 1B, the measurement chamber 100 is longer in the first direction than in the second direction. In this example, the measurement chamber 100 is rectangular in shape with the first direction as a longitudinal direction thereof and the second direction as a transverse direction thereof as seen in top plan view.

The upper electrode base material 21 and lower electrode base material 22 are substrates made of, for example, quartz glass, and are transparent substrates. As shown in FIGS. 2 and 3, the upper electrode base material 21 is disposed on the upper side of the first member 11. The lower electrode base material 22 is disposed on the lower side of the second member 12. As shown in FIGS. 2 and 3, the upper electrode base material 21 has a lower surface that blocks an upper opening of the measurement chamber 100. The lower electrode base material 22 has an upper surface that blocks a lower opening of the measurement chamber 100.

As shown in FIG. 1A, an upper working electrode 40, an upper reference electrode 60, the measurement chamber 100, and the like which are disposed inside the culture device 1 are visible from above because the upper electrode base material 21 is transparent. Similarly, as shown in FIG. 1B, a lower working electrode 50, a lower reference electrode 70, the measurement chamber 100, and the like which are disposed inside the culture device 1 are visible from below because the lower electrode base material 22 is transparent.

As shown in FIGS. 2 and 3, the culture device 1 further includes a permeable layer 30. The permeable layer 30 is a sheet-like permeable membrane that is permeable to liquid. The permeable layer 30 is made of, for example, PC (polycarbonate), PTFE (polytetrafluoroethylene), or PET. The permeable layer 30 is held between the first member 11 and the second member 12.

The permeable layer 30 is a layer that partitions the measurement chamber 100 into a first chamber 110 on the upper side and a second chamber 120 on the lower side as seen in the upward/downward direction. A liquid contained in the measurement chamber 100 is allowed to pass between the first chamber 110 and the second chamber 120 through the permeable layer 30. The first chamber 110 is formed by the inner surface 13a of the first member 11, and the second chamber 120 is formed by the inner surface 13b of the second member 12.

As shown in FIGS. 1A, 1B, and 2, the culture device 1 includes a supply port 210 and the supply flow channel 14. The supply flow channel 14 is a flow passage through which a liquid supplied from the outside into the measurement chamber 100 passes. The supply port 210 is an opening for supplying a liquid from the outside to the supply flow channel 14. In this example, the supply port 210 is formed by a hole that passes through the upper electrode base material 21 in the upward/downward direction. The supply port 210 is in communication with the first chamber 110 of the measurement chamber 100 through the supply flow channel 14. The term "communication" used herein means a state in which components are coupled to each other so as to allow a liquid to pass therebetween. The supply flow channel 14 is in the form of a tube extending in the first direction. As shown in FIG. 2, the supply flow channel 14 is formed by an inner surface of a hole passing upwardly/downwardly through the first member 11, the lower surface of the upper electrode base material 21, and an upper surface of the second member 12.

As shown in FIGS. 1A, 1B, and 2, the culture device 1 includes a discharge port 220 and the discharge flow channel 15. The discharge flow channel 15 is a flow passage through which a liquid discharged from within the measurement chamber 100 to the outside passes. The discharge port 220 is an opening for discharging a liquid from the discharge flow channel 15. In this example, the discharge port 220 is formed by a hole that passes upwardly/downwardly through the upper electrode base material 21 and the first member 11. The discharge port 220 is in communication with the second chamber 120 of the measurement chamber 100 through the discharge flow channel 15. The discharge flow channel 15 is in the form of a tube extending in the first direction. As shown in FIG. 2, the discharge flow channel 15 is formed by an inner surface of a hole passing upwardly/downwardly through the second member 12, a lower surface of the first member 11, and the upper surface of the lower electrode base material 22.

When the culture device 1 is used to measure the electrical resistance of the cells 9, a supply tube for supplying a liquid such as a culture solution to the measurement chamber 100 is connected to the supply port 210, and a discharge tube for discharging the culture solution from the measurement chamber 100 is connected to the discharge port 220.

As shown in FIGS. 1A and 1B, the culture device 1 includes the upper working electrode 40 (a first-side working electrode), the lower working electrode 50 (a second-side working electrode), the upper reference electrode 60 (a first-side reference electrode), and the lower reference electrode 70 (a second-side reference electrode).

The upper working electrode 40 and the upper reference electrode 60 are disposed on the lower surface of the upper electrode base material 21. The upper working electrode 40 and the upper reference electrode 60 are disposed on the upper side (on a first side as seen in the third direction) with respect to the measurement chamber 100. The lower working electrode 50 and the lower reference electrode 70 are disposed on the upper surface of the lower electrode base material 22. The lower working electrode 50 and the lower reference electrode 70 are disposed on the lower side (on a second side as seen in the third direction) with respect to the measurement chamber 100.

The upper working electrode 40 and the upper reference electrode 60 are formed, for example, by depositing metal for electrodes on the lower surface of the upper electrode base material 21. At least part of the upper working and reference electrodes 40 and 60 formed by the metal deposition which overlaps the measurement chamber 100 in the upward/downward direction is preferably covered with an insulating protective film (oxide film). Covering with the insulating protective film in this manner suppresses electrochemical reactions occurring at an interface between the electrode metal and the liquid to thereby suppress degradation and wear of the electrode metal over time. Like the upper working and reference electrodes 40 and 60, the lower working and reference electrodes 50 and 70 are formed by the metal deposition on the upper surface of the lower electrode base material 22 and are covered with an insulating protective film, as appropriate.

<Upper Working Electrode 40>

As shown in FIG. 1A, the upper working electrode 40 includes a working electrode portion 41 (a first first-side working electrode portion), a working electrode portion 42 (a second first-side working electrode portion), and a working bus portion 43. The working electrode portions 41 and 42 are longer in the first direction than in the second direction, as shown in FIG. 1A. In this example, the working electrode portions 41 and 42 extend linearly in the first direction. As shown in FIG. 1A, one end portion of each of the working electrode portions 41 and 42 as seen in the first direction is electrically connected to the working bus portion 43.

As shown in FIGS. 1A and 3, the working electrode portion 42 is spaced from the working electrode portion 41 in the second direction. The working electrode portion 41 is disposed in a position shifted from the middle of the measurement chamber 100 toward the first side in the second direction. The working electrode portion 42 is disposed in a position shifted from the middle of the measurement chamber 100 toward the second side in the second direction.

As shown in FIG. 3, the working electrode portion 41 is spaced a distance W31 toward the second side in the second direction from the first side surface 101 of the measurement chamber 100. The working electrode portion 42 is spaced a distance W32 toward the first side in the second direction from the second side surface 102 of the measurement chamber 100.

<Lower Working Electrode 50>

As shown in FIG. 1B, the lower working electrode 50 includes a working electrode portion 51 (a first second-side working electrode portion), a working electrode portion 52 (a second second-side working electrode portion), and a working bus portion 53. The working electrode portions 51 and 52 are longer in the first direction than in the second direction. In this example, the working electrode portions 51 and 52 extend linearly in the first direction. One end portion of each of the working electrode portions 51 and 52 as seen in the first direction is electrically connected to the working bus portion 53.

As shown in FIGS. 1B and 3, the working electrode portion 52 is spaced from the working electrode portion 51 toward the second side in the second direction. The working electrode portion 51 is disposed in a position shifted from the middle of the measurement chamber 100 toward the first side in the second direction. The working electrode portion 52 is disposed in a position shifted from the middle of the measurement chamber 100 toward the second side in the second direction. As shown in FIG. 3, the working electrode portion 52 is spaced from the working electrode portion 41 toward the second side in the second direction.

As shown in FIG. 3, the working electrode portion 51 is spaced a distance W33 toward the second side in the second direction from the first side surface 101 of the measurement chamber 100. The working electrode portion 52 is spaced a distance W34 toward the first side in the second direction from the second side surface 102 of the measurement chamber 100.

The working electrode portions 41, 42, 51, and 52 have respective widths (dimensions as measured in the second direction) W11, W12, W13, and W14 preferably equal to each other.

As shown in FIG. 3, the working electrode portions 41 and 51 are in the same position as seen in the second direction. In the measurement chamber 100, the working electrode portion 41 faces the working electrode portion 51 in the upward/downward direction. As shown in FIG. 3, the working electrode portions 42 and 52 are in the same position as seen in the second direction. In the measurement chamber 100, the working electrode portion 42 faces the working electrode portion 52 in the upward/downward direction.

The working electrode portions 41, 42, 51, and 52 are in such positions as to overlap the measurement chamber 100 in the upward/downward direction. As shown in FIGS. 1A, 1B, and 2, each of the working electrode portions 41, 42, 51, and 52 is longer in the first direction than the measurement chamber 100. As shown in FIGS. 1A, 1B, and 2, the working electrode portions 41, 42, 51, and 52 are disposed to traverse the measurement chamber 100 in the first direction. In other words, the upper working electrode 40 and the lower working electrode 50 have the electrode portions (the working electrode portions 41, 42, 51, and 52) extending from a first end of the measurement chamber 100 as seen in the first direction to a second end thereof.

<Upper Reference Electrode 60>

As shown in FIGS. 1A and 3, the upper reference electrode 60 includes a reference electrode portion 61 (a first first-side reference electrode portion), a reference electrode portion 62 (a second first-side reference electrode portion), and a reference bus portion 63.

The reference electrode portions 61 and 62 are longer in the first direction than in the second direction, as shown in FIG. 1A. In this example, the reference electrode portions 61 and 62 extend linearly in the first direction. One end portion of each of the reference electrode portions 61 and 62 as seen in the first direction is electrically connected to the reference bus portion 63.

As shown in FIG. 3, the reference electrode portion 61 is disposed in a position shifted from the middle of the measurement chamber 100 toward the first side in the second direction. The reference electrode portion 62 is disposed in a position shifted from the middle of the measurement chamber 100 toward the second side in the second direction.

As shown in FIG. 3, the reference electrode portion 62 is spaced a distance W51 toward the second side in the second direction from the reference electrode portion 61. The reference electrode portions 61 and 62 are disposed between the working electrode portions 41 and 42 as seen in the second direction.

As shown in FIG. 3, the reference electrode portion 61 is spaced a distance W41 toward the second side in the second direction from the working electrode portion 41. The reference electrode portion 62 is spaced a distance W42 toward the first side in the second direction from the working electrode portion 42.

In the culture device 1, a gap is formed between the working electrode portions 41 and 42 and extend throughout the length of the measurement chamber 100 (in the first direction). The reference electrode portions 61 and 62 of the upper reference electrode 60 are disposed in the gap. A gap with the distance W51 is formed between the reference electrode portions 61 and 62. This allows an observer to observe the cells 9 supported by the permeable layer 30 from above the culture device 1 through the gap between the reference electrode portions 61 and 62.

The reference electrode portions 61 and 62 of the upper reference electrode 60 have respective widths (dimensions as measured in the second direction) W21 and W22 preferably smaller than the widths W11 and W12 of the working electrode portions 41 and 42 of the upper working electrode 40. Thus making the widths W21 and W22 of the reference electrode portions 61 and 62 smaller restrains the upper reference electrode 60 from becoming a hindrance to the observation of the cells 9.

<Lower Reference Electrode 70>

The lower reference electrode 70 includes a reference electrode portion 71 (a first second-side reference electrode portion), a reference electrode portion 72 (a second second-side reference electrode portion), and a reference bus portion 73. The reference electrode portions 71 and 72 are longer in the first direction than in the second direction. In this example, the reference electrode portions 71 and 72 extend linearly in the first direction. One end portion of each of the reference electrode portions 71 and 72 as seen in the first direction is electrically connected to the reference bus portion 73.

Although not shown in FIGS. 1A and 1B, the working bus portions 43 and 53 and the reference bus portions 63 and 73 have contact portions for electrical connection to external devices. The contact portions are exposed to the outside of the culture device 1 so as to allow electrodes (such as probe pins) of the external devices to come in contact with the contact portions.

As shown in FIG. 3, the reference electrode portion 71 is disposed in a position shifted from the middle of the measurement chamber 100 toward the first side in the second direction. The reference electrode portion 72 is disposed in a position shifted from the middle of the measurement chamber 100 toward the second side in the second direction.

As shown in FIG. 3, the reference electrode portion 72 is spaced a distance W52 toward the second side in the second direction from the reference electrode portion 71. The reference electrode portions 71 and 72 are disposed between the working electrode portions 51 and 52 as seen in the second direction.

As shown in FIG. 3, the reference electrode portions 61 and 71 are in the same position as seen in the second direction. In the measurement chamber 100, the reference electrode portion 61 faces the reference electrode portion 71 in the upward/downward direction. As shown in FIG. 3, the reference electrode portions 62 and 72 are in the same position as seen in the second direction. In the measurement chamber 100, the reference electrode portion 62 faces the reference electrode portion 71 in the upward/downward direction.

The widths W21, W22, W23, and W24 of the respective reference electrode portions 61, 62, 71, and 72 are preferably equal to each other. The widths W23 and W24 of the respective reference electrode portions 71 and 72 are preferably smaller than the widths W13 and W14 of the respective working electrode portions 51 and 52 of the lower working electrode 50.

In the measurement chamber 100, the reference electrode portion 61 and the reference electrode portion 71 overlap (or coincide with} each other in the upward/downward direction, and the reference electrode portion 62 and the reference electrode portion 72 overlap (or coincide with} each other in the upward/downward direction. Each of the reference electrode portions 61, 62, 71, and 72 is longer in the first direction than the measurement chamber 100. As shown in FIGS. 1A and 1B, the reference electrode portions 61, 62, 71, and 72 are disposed to traverse the measurement chamber 100 in the first direction. In other words, the upper reference electrode 60 and the lower reference electrode 70 have the electrode portions (the reference electrode portions 61, 62, 71, and 72) extending from the first end of the measurement chamber 100 as seen in the first direction to the second end thereof.

The measurement chamber 100 is preferably not greater than 100 mm and more preferably in the range of 20 to 30 mm in dimension measured in the first direction. The measurement chamber 100 is preferably not greater than 10 mm and more preferably in the range of 1 to 2 mm in dimension measured in the second direction. The measurement chamber 100 is preferably not greater than 10 mm and more preferably in the range of 1 to 2 mm in dimension measured in the upward/downward direction.

The widths W11, W12, W13, and W14 of the respective working electrode portions 41, 42, 51, and 52 are preferably not greater than 1 mm, more preferably in the range of 300 to 500 µm, and exemplarily 400 µm. The widths W11, W12, W13, and W14 are preferably equal to each other, but may be different from each other.

As shown in FIG. 3, the widths W21, W22, W23, and W24 of the respective reference electrode portions 61, 62, 71, and 72 are preferably not greater than 200 µm, more preferably in the range of 50 to 150 µm, and exemplarily 100 µm. The widths W21, W22, W23, and W24 are preferably equal to each other, but may be different from each other.

As shown in FIG. 3, the distance W31 between the working electrode portion 41 and the first side surface 101, the distance W32 between the working electrode portion 42 and the second side surface 102, the distance W33 between the working electrode portion 51 and the first side surface 101, and the distance W34 between the working electrode portion 52 and the second side surface 102 are preferably in the range of 100 to 300 µm, and exemplarily 200 µm. The distances W31, W32, W33, and W34 are preferably equal to each other, but may be different from each other.

As shown in FIG. 3, the distance W41 between the working electrode portion 41 and the reference electrode portion 61, the distance W42 between the working electrode portion 42 and the reference electrode portion 62, a distance W43 between the working electrode portion 51 and the reference electrode portion 71, and a distance W44 between the working electrode portion 52 and the reference electrode portion 72 are preferably not greater than 200 μm, and exemplarily 100 μm. The distances W41, W42, W43, and W44 are preferably equal to each other, but may be different from each other.

As shown in FIG. 3, the distance W51 between the reference electrode portions 61 and 62, and the distance W52 between the reference electrode portions 71 and 72 are preferably in the range of 300 to 500 μm, and exemplarily 400 μm. The distances W51 and W52 are preferably equal to each other, but may be different from each other.

The area of the working electrode portions 41 and 42 of the upper working electrode 40 which overlap the measurement chamber 100 as seen in top plan view is preferably in the range of 30% to 50% of the area of the measurement chamber 100, and exemplarily 40% thereof.

<Measurement of Electrical Resistance>

Figure 4:
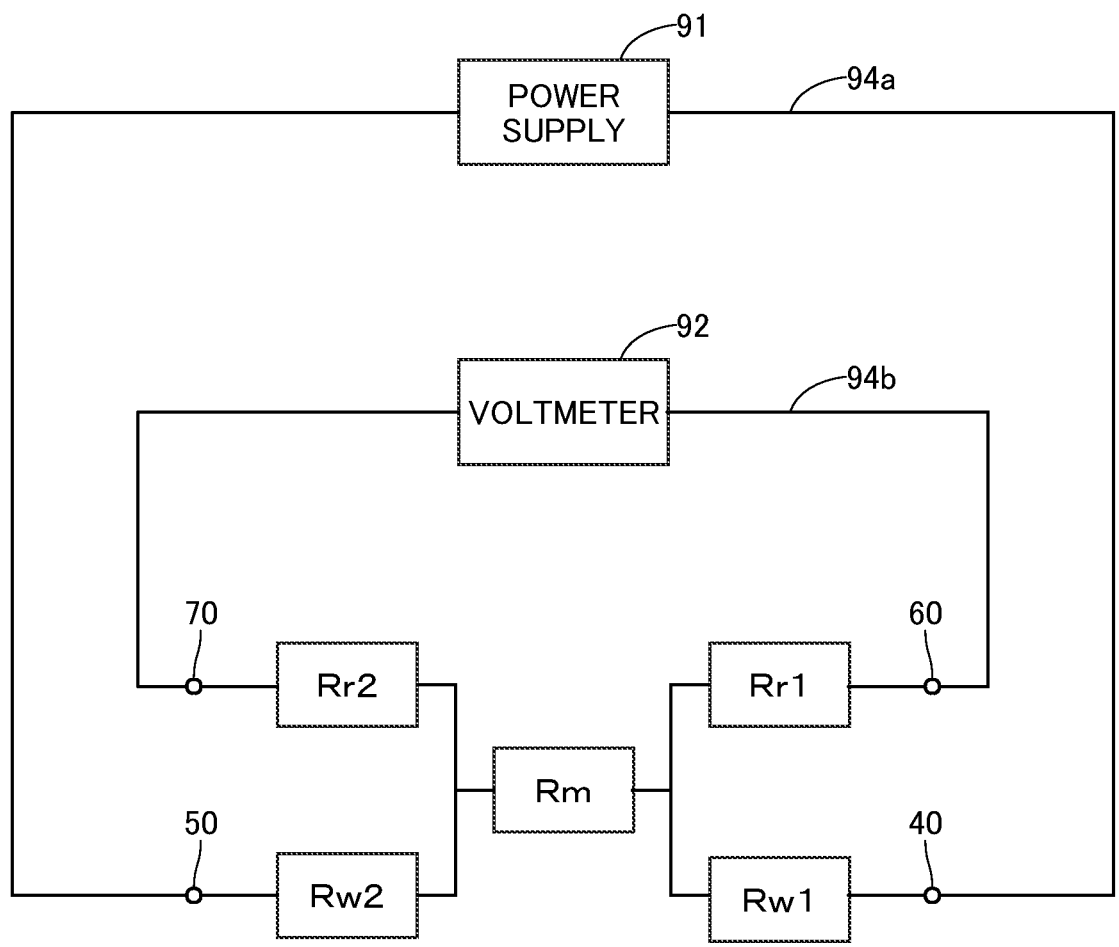
FIG. 4 is a circuit diagram for measurement of the resistance of cells.

FIG. 4 is a circuit diagram for measurement of the electrical resistance of the cells 9. For the measurement of the electrical resistance of the cells 9, a power supply device 91 and a voltmeter 92 are connected to the culture device 1. The power supply device 91 has an output terminal electrically connected through a conductor 94a to a contact portion of the upper working electrode 40 and to a contact portion of the lower working electrode 50. The voltmeter 92 has an input terminal electrically connected through a conductor 94b to a contact portion of the upper reference electrode 60 and to a contact portion of the lower reference electrode 70.

For the measurement of the electrical resistance of the cells 9, the cells 9 which are large in number are supported on the upper surface of the permeable layer 30 in the measurement chamber 100. Then, the measurement chamber 100 is filled with a liquid such as the culture solution through the supply port 210 and the supply flow channel 14. Also, the liquid in the measurement chamber 100 is discharged through the discharge port 220 and the discharge flow channel 15. This results in the exchange (or circulation) of the liquid in the first and second chambers 110 and 120 of the measurement chamber 100.

With reference to FIG. 4, a resistance Rm corresponds to the electrical resistance of a portion of the permeable layer 30 which is disposed in the measurement chamber 100 and a layer of the cells 9 (referred to hereinafter as a "cell layer 90") supported by the portion of the permeable layer 30. A resistance Rw1 corresponds to the electrical resistance of the liquid between the upper working electrode 40 and the cell layer 90 (i.e. in the first chamber 110). A resistance Rw2 corresponds to the electrical resistance of the liquid between the lower working electrode 50 and the cell layer 90 (i.e. in the second chamber 120).

With reference to FIG. 4, a resistance Rr1 corresponds to the electrical resistance of the liquid between the upper reference electrode 60 and the cell layer 90 (i.e. in the first chamber 110). A resistance Rr2 corresponds to the electrical resistance of the liquid between the lower reference electrode 70 and the cell layer 90 (i.e. in the second chamber 120).

Current is applied between the upper working electrode 40 and the lower working electrode 50 by the power supply device 91, and voltage between the upper reference electrode 60 and the lower reference electrode 70 is measured by the voltmeter 92. The electrical resistance between the upper working electrode 40 and the lower working electrode 50 is calculated from the voltage value measured by the voltmeter 92. Further, the resistance Rm of the cell layer 90 is calculated from the calculated electrical resistance between the upper working electrode 40 and the lower working electrode 50.

When the power supply device 91 applies the current between the upper working electrode 40 and the lower working electrode 50, the oxidation and reduction reactions of the liquid occur on surfaces of the upper working electrode 40 and the lower working electrode 50 to form an electric double layer in some cases. In such a case, there is apprehension that an output voltage caused by the power supply device 91 and the voltage applied between the upper working electrode 40 and the lower working electrode 50 differ from each other. In the culture device 1, the upper reference electrode 60 and the lower reference electrode 70 are disposed in the vicinity of the upper working electrode 40 and the lower working electrode 50, respectively, in the measurement chamber 100. Thus, the voltage between the upper reference electrode 60 and the lower reference electrode 70 is measured, and the measured voltage is used as the voltage between the upper working electrode 40 and the lower working electrode 50, whereby the resistance Rm of the cell layer 90 is measured accurately.

<Effects>

In the culture device 1, the dimensions of the electrode portions facing the measurement chamber 100 are made longer by extending the upper and lower working electrodes 40 and 50 in the first direction that is the longitudinal direction of the measurement chamber 100 than by extending the electrodes 40 and 50 in the transverse direction of the measurement chamber 100. This increases the area to which the current is applied without increasing the number of electrodes and without making the electrodes thicker. Thus, the current is effectively applied to a wide area of the measurement chamber 100 while the upper working electrode 40 is restrained from becoming a hindrance to the observation of the cells 9.

The upper working electrode 40 has the electrode portions (the working electrode portions 41 and 42) extending from the first end of the measurement chamber 100 as seen in the first direction to the second end thereof. This allows the current to be applied to the entire longitudinal area of the measurement chamber 100, thereby allowing the current to be applied to a wide area of the measurement chamber 100. In addition, the lower working electrode 50 has the electrode portions (the working electrode portions 51 and 52) extending from the first end of the measurement chamber 100 as seen in the first direction to the second end thereof. This allows the current to be applied to the entire longitudinal area of the measurement chamber 100.

The current is applied to the cells 9 present between the working electrode portions 41 and 51 because the working electrode portions 41 and 51 face each other. Also, the current is applied to the cells 9 present between the working electrode portions 42 and 52 because the working electrode portions 42 and 52 face each other.

The working electrode portion 52 is spaced from the working electrode portion 41 in the second direction. Thus, the current flows between the working electrode portions 41 and 52, whereby the current is applied to an intermediate portion of the cell layer 90. Similarly, the current flows between the working electrode portions 42 and 51, whereby the current is applied to the intermediate portion of the cell layer 90.

The culture device 1 includes the first member 11, the second member 12, the upper electrode base material 21, the lower electrode base material 22, and the permeable layer 30. Thus, the measurement chamber 100 with the pair of upper and lower working electrodes 40 and 50 disposed on both sides is easily formed by stacking these members 11, 12, 21, 22 and 30 vertically in a predetermined order.

<Simulation>

Figure 5A:
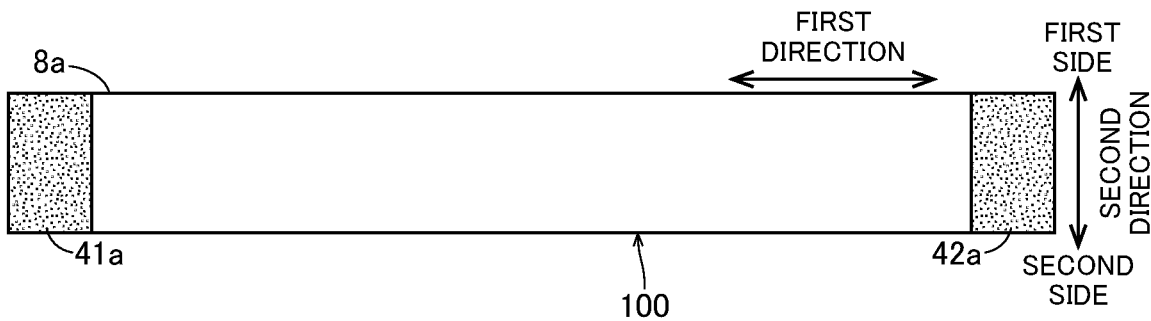
FIGS. 5A to 5C show simulation results of current density using an analytical model according to a comparative example.
Figure 5B:
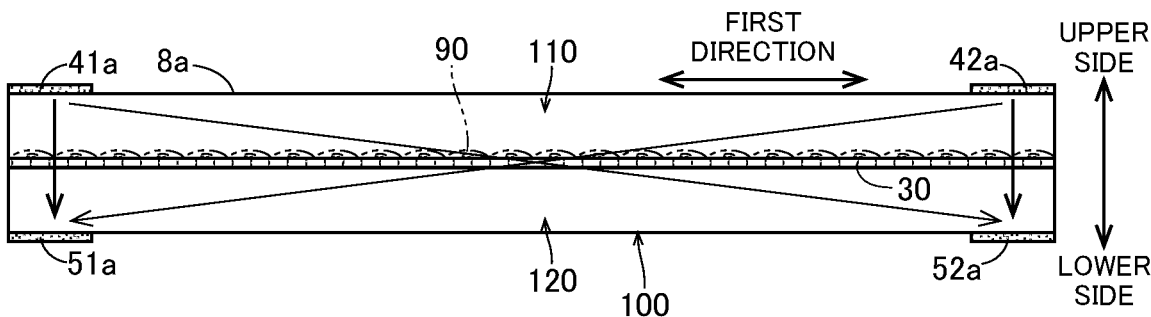
Figure 5C:
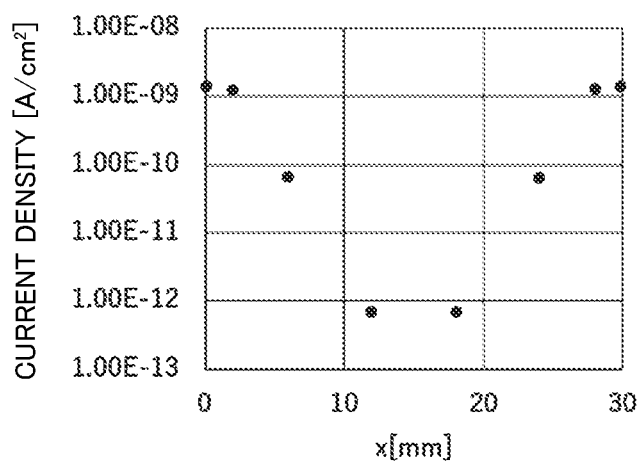

FIGS. 5A to 5C show simulation results of current density using an analytical model 8a according to a comparative example. FIGS. 6A to 6D show simulation results of current density using an analytical model 8b corresponding to the culture device 1 shown in FIGS. 1A and 1B. The simulation of the current density is specifically performed by the finite element method using analysis software such as COMSOL Multiphysics (available from COMSOL AB). In the analytical models 8a and 8b, the measurement chamber 100 is 30 mm in dimension measured in the first direction (longitudinal direction), 1 mm in dimension measured in the second direction (transverse direction), and 1 mm in dimension measured in the upward/downward direction. In FIGS. 5A to 5C and FIGS. 6A to 6D, the electrical resistance of the cell layer 90 is uniform throughout the entire area. For purposes of simplifying the simulation, the analytical models 8a and 8b include only the upper working electrode 40 and the lower working electrode 50, and the upper reference electrode 60 and the lower reference electrode 70 are dispensed with.

FIG. 5A is a top view of the analytical model 8a, and FIG. 5B is a side view of the analytical model 8a. FIG. 5C is a graph showing the simulation results of the current density. In FIG. 5C, the abscissa represents the position (mm) of the measurement chamber 100 as measured in the first direction, and the ordinate represents the current density (A/cm$^2$).

In the analytical model 8a according to the comparative example, the upper working electrode 40 and the lower working electrode 50 include electrode portions (working electrode portions 41a, 42a, 51a, and 52a) which are longer in the second direction than in the first direction and which are disposed on both end portions of the measurement chamber 100 as seen in the first direction, as shown in FIGS. 5A and 5B. The working electrode portions 41a and 51a face each other in the upward/downward direction, and the working electrode portions 42a and 52a face each other in the upward/downward direction.

In the analytical model 8a, the current density decreases toward the middle of the measurement chamber 100 in the first direction, as shown in FIG. 5C. Specifically, the current density immediately under the electrode is approximately $1.00 \times 10^{-9}$, whereas the current density near the middle of the measurement chamber 100 is approximately $1.00 \times 10^{-12}$. There is a difference of approximately 1000 times between these current density values. In other words, the electrode configuration as in the analytical model 8a causes large variations in current density.

Figure 6A:
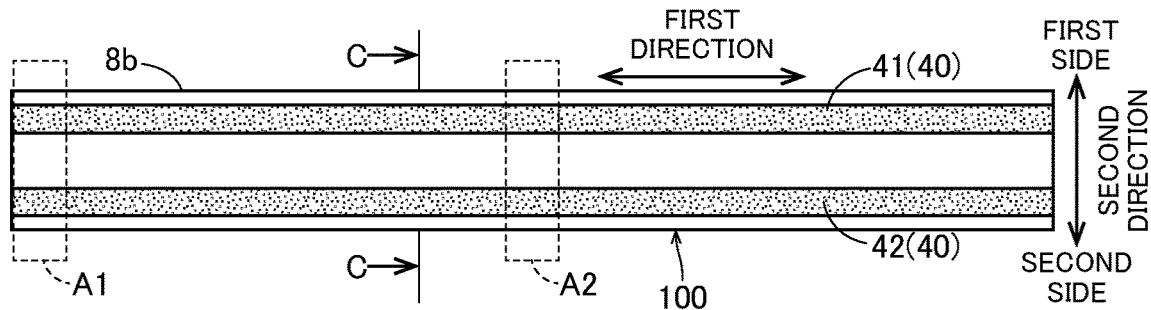
FIGS. 6A to 6D show simulation results of current density using an analytical model corresponding to the culture device shown in FIGS. 1A and 1B.
Figure 6B:
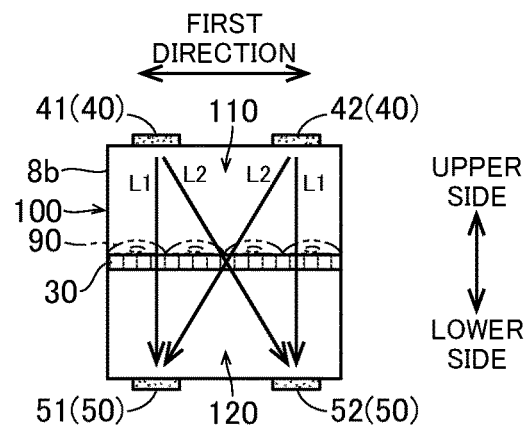
Figure 6C:
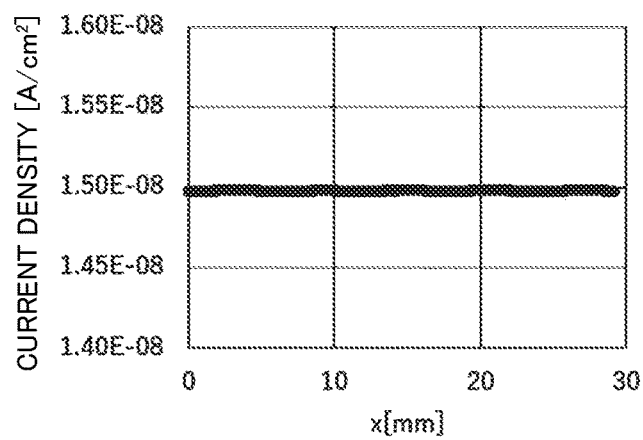
Figure 6D:
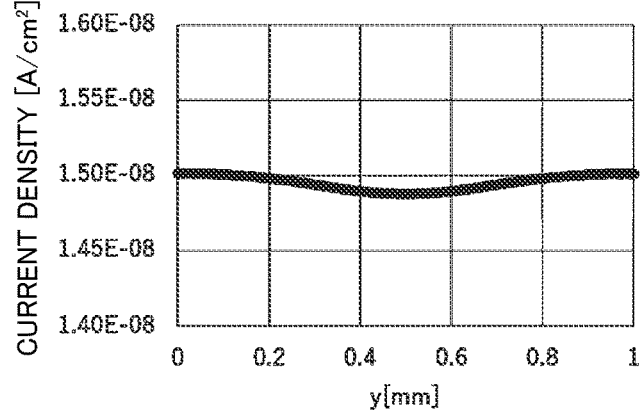

FIG. 6A is a top view of the analytical model 8b, and FIG. 6B is a sectional view of the analytical model 8b taken along a line C-C of FIG. 6A. FIGS. 6C and 6D are graphs showing the simulation results of the current density. In FIG. 6C, the abscissa represents the position (mm) of the measurement chamber 100 as measured in the first direction, and the ordinate represents the current density (A/cm$^2$). In FIG. 6D, the abscissa represents the position (mm) of the measurement chamber 100 as measured in the second direction, and the ordinate represents the current density (A/cm$^2$).

In the analytical model 8b, there is almost no variation in current density in the first direction, as shown in FIG. 6C. In the analytical model 8b, a difference in current density is less than 5% in the second direction, as shown in FIG. 6D. These simulation results show that the electrode configuration in the analytical model 8b allows the current to be uniformly applied to the whole of the cells 9.

In the analytical model 8b, a distance L2 (a second distance) between the working electrode portions 41 and 52 is sufficiently small relative to a distance L1 (a first distance; 1 mm in this case) between the working electrode portions 41 and 51. Thus, sufficient current flows between the working electrode portions 41 and 52. Also, sufficient current flows between the working electrode portions 42 and 51 as well as between the working electrode portions 41 and 52. For this reason, the current density is considered to be uniform in the second direction, as shown in FIG. 6D.

It is desirable that the distance L2 is 1.5 times the distance L1. If the distance L2 is greater than 1.5 times the distance L1, the working electrode portion 52 is farther away from the working electrode portion 41 in the second direction. This makes the density of current applied to the cells 9 between the working electrode portions 41 and 52 significantly smaller than the density of current applied to the cells 9 between the working electrode portions 41 and 51. Thus, there is apprehension that variations occur in density of current applied to the cell layer 90.

FIG. 7 shows the resistances of the cell layer 90 calculated from simulation using the analytical model 8b of FIGS. 6A to 6D. FIG. 7 shows the following resistances: a resistance calculated from simulation on the condition that the resistance of the cell layer 90 is uniform throughout the entire area; resistances calculated from simulation on the condition that the resistance of a region A1 at a first end of the cell layer 90 as seen in the first direction is set to ¹⁄₁₀ and ¹⁄₁₀₀ that of other regions; and resistances calculated from simulation on the conditions that the resistance of a region A2 in the middle of the cell layer 90 as seen in the first direction is set to ¹⁄₁₀ and ¹⁄₁₀₀ that of other regions.

As shown in FIG. 7, when the resistances of the region A1 at the first end and the region A2 in the middle are set to ¹⁄₁₀, the calculated resistances are 197.5Ω and 197.9Ω, respectively. When the resistances of the region A1 at the first end and the region A2 in the middle are set to ¹⁄₁₀₀, the calculated resistances are 190.6Ω and 191.3Ω, respectively. Thus, in the case of the analytical model 8b, the resistances of the cell layer 90 calculated from the current density are approximately the same even if the resistance of either the region A1 at the first end of the cell layer 90 or the region A2 in the middle thereof is varied.

In the case of the analytical model 8a, there are variations in current density between end portions of the cell layer 90 and the vicinity of the middle thereof, as shown in FIG. 5C. Accordingly, there can arise a difference in resistance of the cell layer 90 calculated from the current density between the instance where the resistance of the region A1 at the first end of the cell layer 90 is lowered and the instance where the resistance of the region A2 in the middle of the cell layer 90 is lowered. In the case of the analytical model 8b, on the other hand, the current density is uniform in the first direction, as shown in FIG. 6C. For this reason, even if a portion of the cell layer 90 is low in resistance, current flows uniformly to other portions. Thus, even when a portion different in resistance from its surroundings is in any position in the cell layer 90, current is applied uniformly to other portions of the cell layer 90, so that the same level of resistance is finally calculated. Therefore, the electrode configuration of the analytical model 8b achieves improvements in reproducibility of TEER measurement, as compared with the electrode configuration of the analytical model 8a.

As described above, the analysis result of the analytical model 8b shows that current is uniformly applied to a wide area of the cell layer 90 by extending the working electrode portions 41, 42, 51, and 52 in the longitudinal direction of the measurement chamber 100. In addition, even if the resistance of a portion of the cell layer 90 is varied due to the death or lack of some of the cells 9, current flows uniformly to other portions of the cell layer 90. This allows the appropriate calculation of the resistance of the cell layer 90.

2. Modifications

While the preferred embodiment according to the present invention has been described hereinabove, the present invention is not limited to the aforementioned preferred embodiment, but various modifications may be made.

Figure 8:
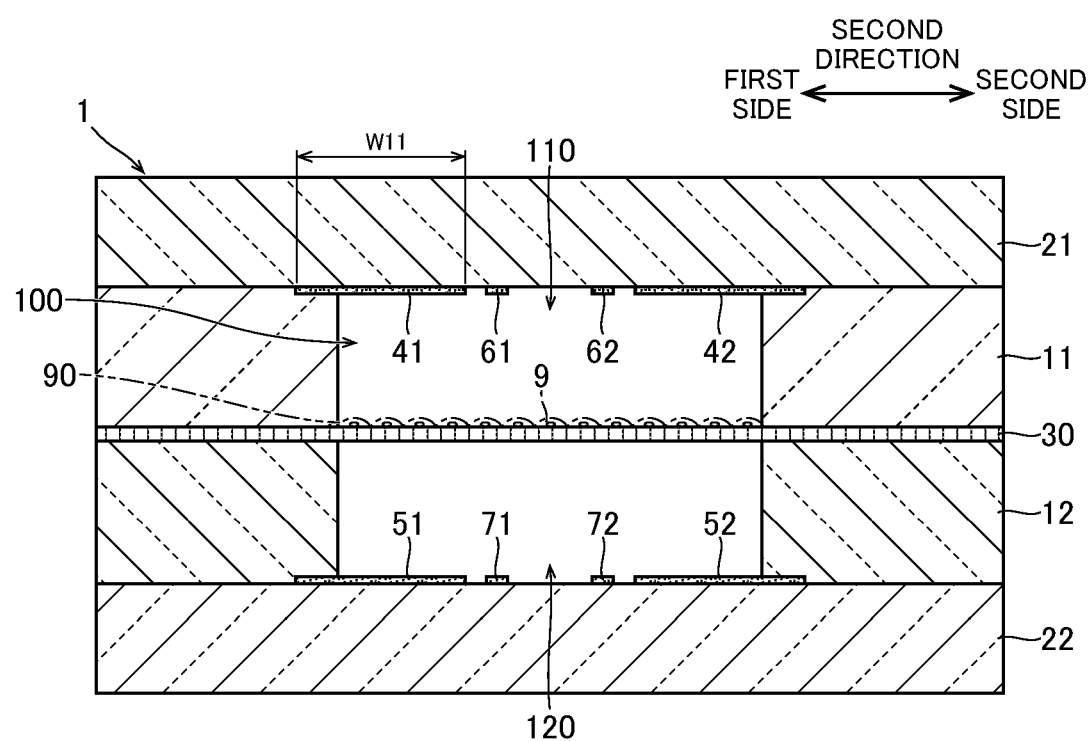
FIG. 8 is a sectional view of the culture device according to a first modification.

FIG. 8 is a sectional view of the culture device 1 according to a first modification. As shown in FIG. 8, the working electrode portions 41 and 42 of the upper working electrode 40 may extend in the second direction to the outside of the measurement chamber 100. In this first modification, the width W11 of the working electrode portion 41 is 800 µm, for example. Thus extending the working electrode portions 41 and 42 to the outside of the measurement chamber 100 allows current to be applied to end portions of the measurement chamber 100 as seen in the second direction. As shown in FIG. 8, the working electrode portions 51 and 52 of the lower working electrode 50 may also extend in the second direction to the outside of the measurement chamber 100.

Figure 9:
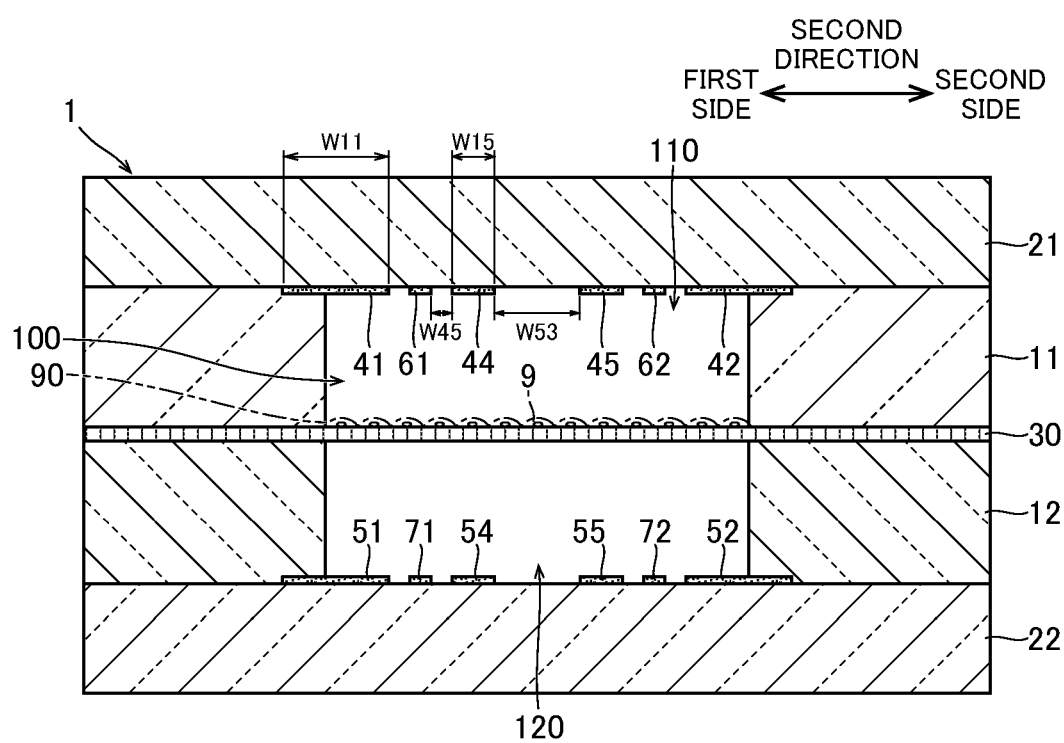
FIG. 9 is a sectional view of the culture device according to a second modification.

FIG. 9 is a sectional view of the culture device 1 according to a second modification. As shown in FIG. 9, the upper working electrode 40 may further include working electrode portions 44 and 45 in addition to the working electrode portions 41 and 42. The working electrode portions 44 and 45 extend linearly in the first direction.

The reference electrode portion 61 is disposed between the working electrode portions 41 and 44 as seen in the second direction. The reference electrode portion 62 is disposed between the working electrode portions 42 and 45 as seen in the second direction. In this second modification, the width W11 of the working electrode portion 41 is 500 µm, for example. The working electrode portion 44 has a width W15 of 200 µm, for example. A distance W45 between the reference electrode portion 61 and the working electrode portion 44 is 100 µm, for example. A distance W53 between the working electrode portions 44 and 45 is 400 µm, for example.

As shown in FIG. 9, the lower working electrode 50 may further include working electrode portions 54 and 55 in addition to the working electrode portions 51 and 52. The working electrode portions 54 and 55 extend linearly in the first direction. The reference electrode portion 71 may be disposed between the working electrode portions 51 and 54 as seen in the second direction. The reference electrode portion 72 may be disposed between the working electrode portions 52 and 55 as seen in the second direction.

While the invention has been shown and described in detail, the foregoing description is in all aspects illustrative and not restrictive. It is therefore understood that numerous modifications and variations can be devised without departing from the scope of the invention. The components described in the aforementioned preferred embodiment and in the various modifications may be combined together or dispensed with, as appropriate, unless the components are inconsistent with each other.

What is claimed is:

1. A culture device applicable to measurement of an electrical resistance of a culture, the culture device comprising:
   a measurement chamber longer in a first direction than in a second direction intersecting said first direction;
   a permeable layer partitioning said measurement chamber into a first chamber on a first side and a second chamber on a second side as seen in a third direction, said third direction intersecting said first and second directions, said permeable layer being permeable to liquid;
   a first-side working electrode disposed on the first side as seen in said third direction with respect to said measurement chamber, and having an electrode portion longer in said first direction than in said second direction;
   a second-side working electrode disposed on the second side as seen in said third direction with respect to said measurement chamber, and having an electrode portion longer in said first direction than in said second direction; and
   a first-side reference electrode disposed on the first side as seen in said third direction with respect to said measurement chamber, and having an electrode portion longer in said first direction than in said second direction,
   wherein said first-side working electrode includes:
      a first first-side working electrode portion including a first end portion and a second end portion such that the first first-side working electrode extends in said first direction from the first end portion to the second end portion;
      a second first-side working electrode portion including a third end portion and a fourth end portion such that the second first-side working electrode extends in said first direction from the third end portion to the fourth end portion, the second first-side working electrode being spaced from said first first-side working electrode portion in said second direction; and
      a first-side working bus portion extending in said second direction and electrically connected to the first end portion of said first first-side working electrode portion and to the third end portion of said second first-side working electrode portion,
   wherein said first-side reference electrode is disposed between said first first-side working electrode portion and said second first-side working electrode portion in said second direction,
   wherein said first-side reference electrode has a width smaller than widths of said first first-side working electrode portion and said second first-side working electrode portions, and
   wherein said first first-side working electrode portion and said second first-side working electrode portion extend in said second direction to said outside of said measurement chamber.

2. The culture device according to claim 1,
   wherein said second-side working electrode has a first second-side working electrode portion extending in said first direction and facing said first-side working electrode in said measurement chamber.

3. The culture device according to claim 1,
   wherein said second-side working electrode has a second second-side working electrode portion extending in said first direction and spaced from said first-side working electrode in said second direction in said measurement chamber.

4. The culture device according to claim 1,
wherein said second-side working electrode includes:
a first second-side working electrode portion extending in said first direction; and
a second second-side working electrode portion extending in said first direction and spaced from said first second-side working electrode portion in said second direction.

5. The culture device according to claim 4,
wherein said first first-side working electrode portion faces said first second-side working electrode portion in said measurement chamber.

6. The culture device according to claim 5,
wherein said second first-side working electrode portion faces said second second-side working electrode portion in said measurement chamber.

7. The culture device according to claim 4,
wherein a second distance is 1.5 times a first distance, said first distance being a distance between said first first-side working electrode portion and said first second-side working electrode portion, said second distance being a distance between said first first-side working electrode portion and said second second-side working electrode portion.

8. The culture device according to claim 1, further comprising:
a second-side reference electrode disposed on the second side as seen in said third direction with respect to said measurement chamber, and having an electrode portion longer in said first direction than in said second direction.

9. The culture device according to claim 1, further comprising:
a first member having an inner surface forming said first chamber;
a second member disposed on the second side as seen in said third direction with respect to said first member and having an inner surface forming said second chamber;
a first-side electrode base material disposed on the first side as seen in said third direction with respect to said first member and having a surface on which said first-side working electrode is disposed; and
a second-side electrode base material disposed on the second side as seen in said third direction with respect to said second member and having a surface on which said second-side working electrode is disposed,
said permeable layer being disposed between said first member and said second member.

10. The culture device according to claim 1,
wherein said first-side working electrode has an electrode portion extending from a first end of said measurement chamber to a second end thereof as seen in said first direction, and
wherein said second-side working electrode has an electrode portion extending from the first end of said measurement chamber to the second end thereof as seen in said first direction.

* * * * *